United States Patent [19]
Iida

[11] Patent Number: 5,674,181
[45] Date of Patent: Oct. 7, 1997

[54] ENDOSCOPE WITH A DETACHABLE TIP COVER

[75] Inventor: Yoshihiro Iida, Hachioji, Japan

[73] Assignee: Olympus Optical Co., Ltd., Tokyo, Japan

[21] Appl. No.: 578,486

[22] Filed: Dec. 26, 1995

[30] Foreign Application Priority Data

Dec. 27, 1994 [JP] Japan ............................ 6-326326

[51] Int. Cl.⁶ .................................................. A61B 1/04
[52] U.S. Cl. ................... 600/127; 600/121; 600/125; 600/129
[58] Field of Search ........................ 600/121, 122, 600/123, 124, 125, 127, 129, 134, 175, 176

[56] References Cited

U.S. PATENT DOCUMENTS

| | | | |
|---|---|---|---|
| 1,727,495 | 9/1929 | Wappler | 600/127 X |
| 4,646,722 | 3/1987 | Silverstein et al. | |
| 5,262,727 | 11/1993 | Behbin et al. | |
| 5,386,817 | 2/1995 | Jones | 600/125 X |
| 5,415,157 | 5/1995 | Welcome | 600/121 |
| 5,429,118 | 7/1995 | Cole et al. | 600/121 |
| 5,518,501 | 5/1996 | Oneda et al. | 600/127 |

FOREIGN PATENT DOCUMENTS

| | | | |
|---|---|---|---|
| 51-103891 | 8/1976 | Japan . | |
| 64-6804 | 2/1989 | Japan | 600/127 |
| 2-43488 | 9/1990 | Japan . | |
| 2-54734 | 11/1990 | Japan . | |
| 4-146717 | 5/1992 | Japan | 600/127 |
| 4-314439 | 11/1992 | Japan . | |
| 6-118153 | 4/1994 | Japan . | |

Primary Examiner—Beverly M. Flanagan
Attorney, Agent, or Firm—Morgan, Lewis and Bockius LLP

[57] ABSTRACT

The improved endoscope has a detachable tip cover 15 which has at the distal end a tip forming member 5 and a forceps holder 19 that is pivotally mounted in said tip forming member 5, said detachable tip cover 15 being made of an elastic material and detachably mounted over the distal end in such a way as to cover at least part thereof; the endoscope also has means for mounting said detachable tip cover 15 over said distal end and is characterized in that said tip cover 15 is provided with a reinforcement member 28 in the inside, said reinforcement member 28 having an engagement hole 32 which engages a corresponding projection 31 on the tip forming member 5.

63 Claims, 9 Drawing Sheets

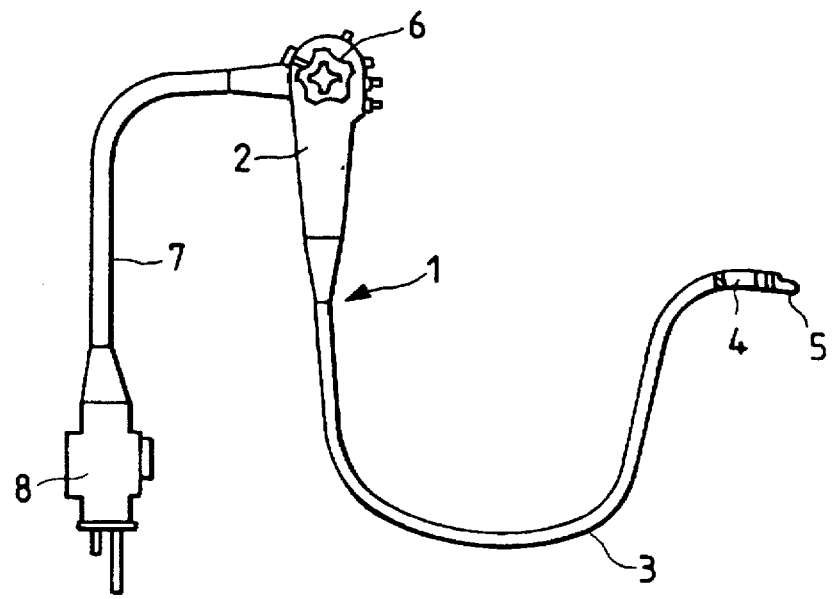
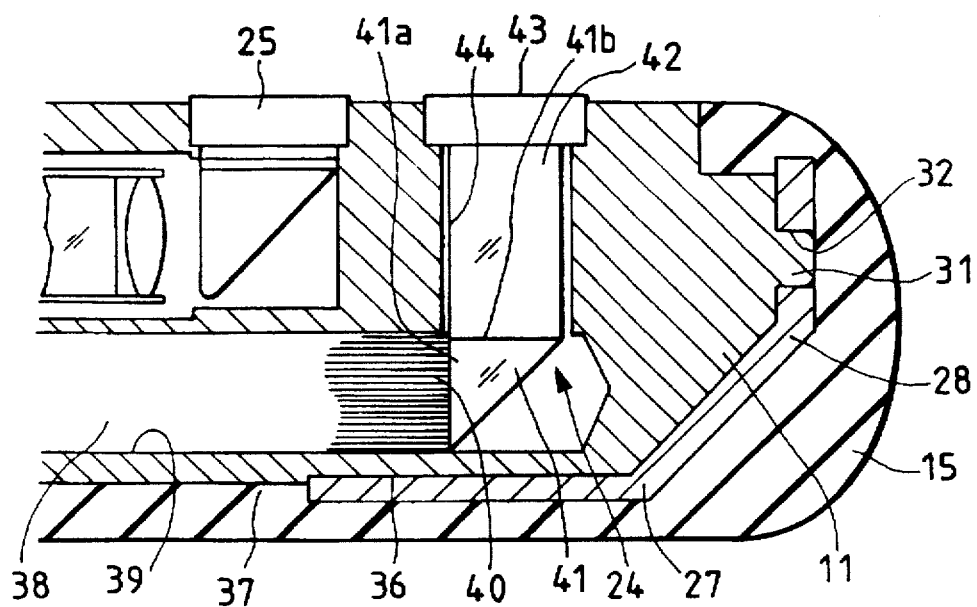

FIG. 5(a)
FIG. 5(b)
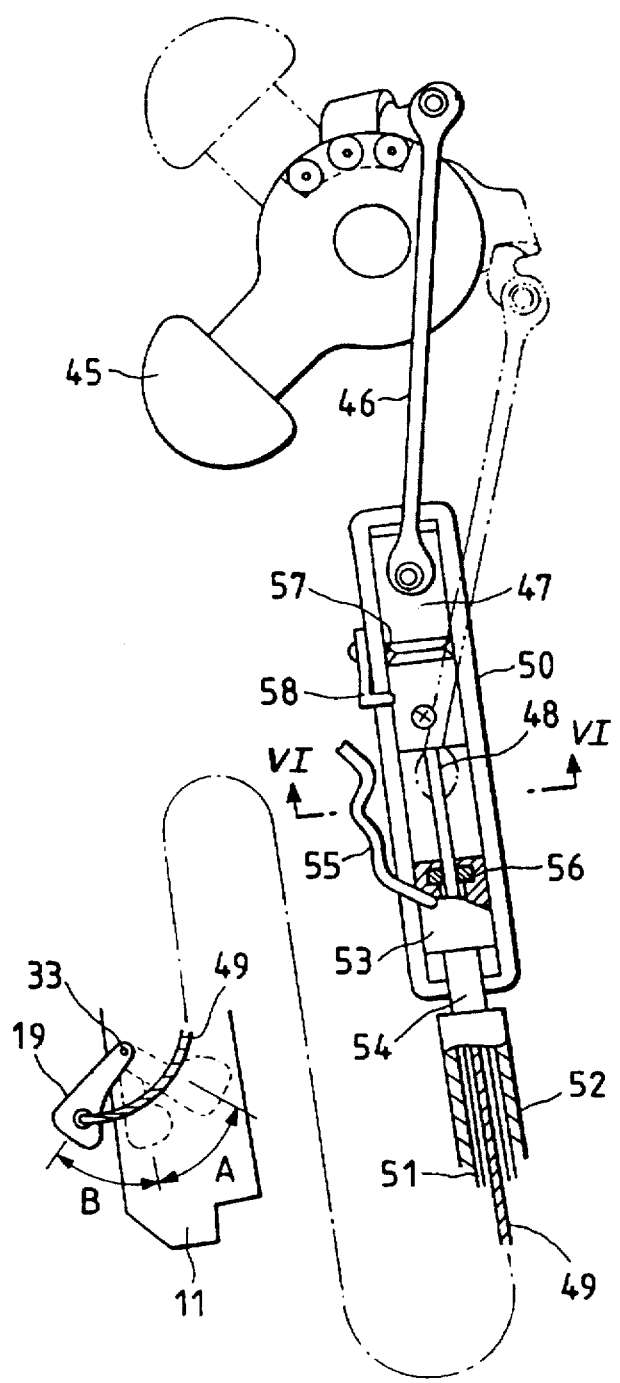
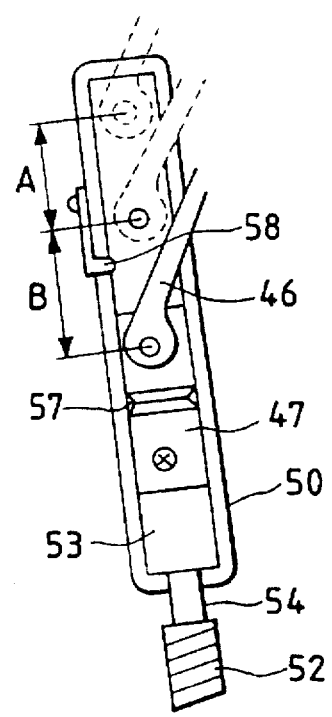

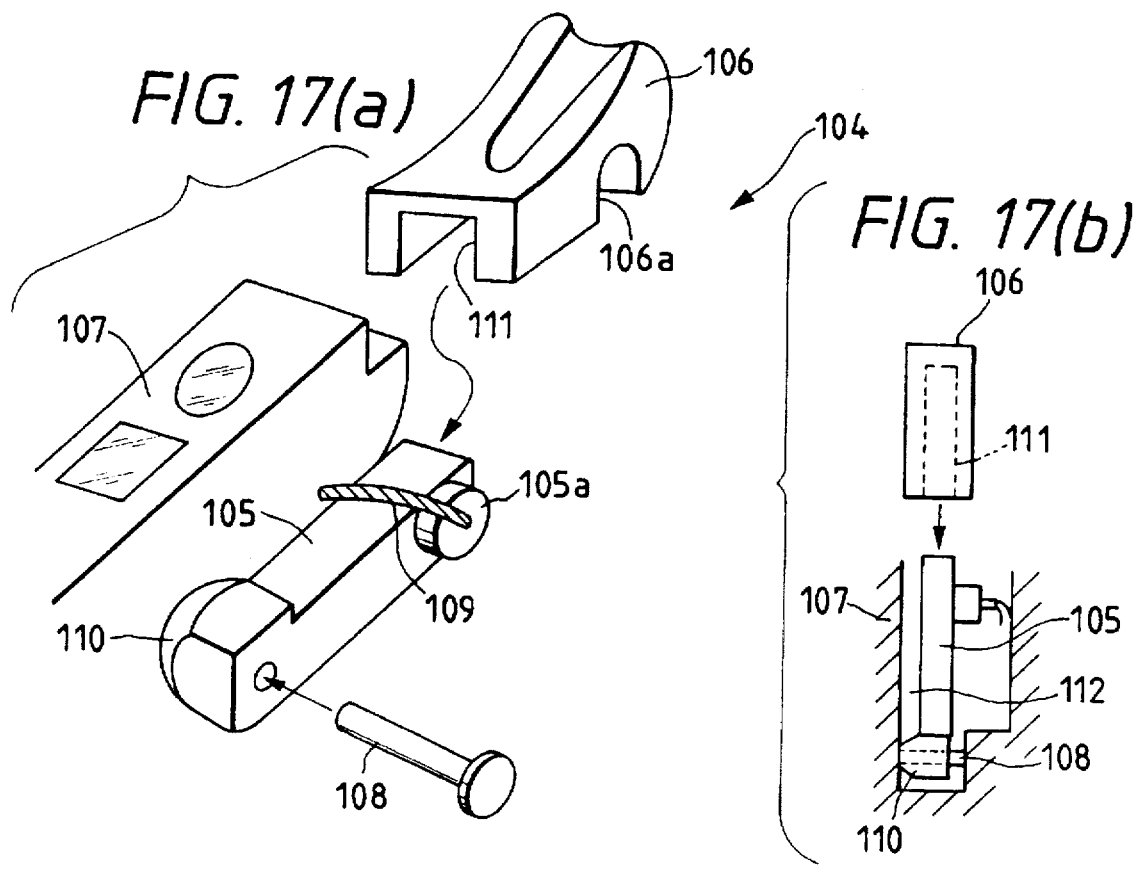
FIG. 17(a)
FIG. 17(b)
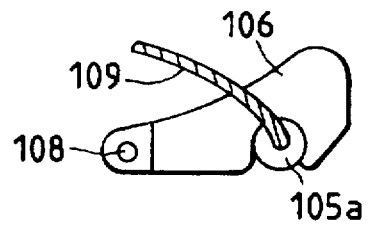
FIG. 17(c)
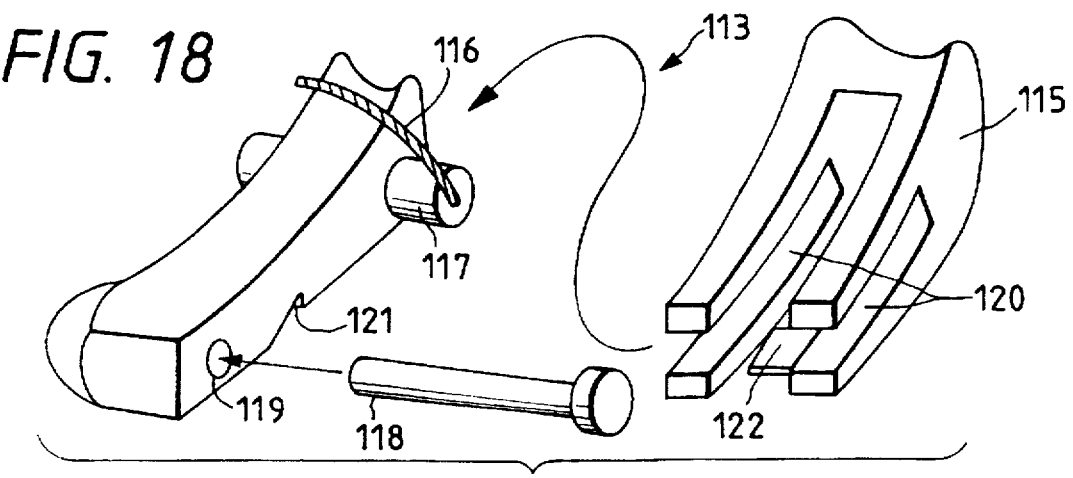
FIG. 18

ENDOSCOPE WITH A DETACHABLE TIP COVER

BACKGROUND OF THE INVENTION

FIELD OF THE INVENTION

The present invention relates to an endoscope having a detachable cover mounted at the distal end.

RELATED ART

Various types of endoscopes are known. For example, unexamined Published Japanese Patent Application (kokai) Hei. 4-314439 teaches a right-angle viewing endoscope that has a tip cover mounted detachably at the distal end of an insertion member inserted into a tubular cavity or canal in the human body. The tip cover is typically formed of a comparatively rigid material.

Unexamined Published Japanese Utility Model Application (kokai) Sho. 51-103891 teaches an elastic cover for all part of the insertion member inserted into a tubular cavity. Examined Japanese Patent Publication (kokoku) Hei. 2-54734 teaches a channeled cover of the insertion member inserted into a tubular cavity.

However, these conventional endoscopes have had various problems. First, not only the members covering of the curved portion upstream of the tip forming member of an endoscope but also comparatively soft parts such as the flexible tubular portion can potentially be scratched, pierced or otherwise damaged as the tip cover is mounted on or dismounted from the tip forming member.

On the other hand, the endoscopes of Unexamined Published Japanese Utility Model Sho. 51-103891 and Examined Published Japanese Patent Publication Hei. 2-54734 which use a cover that surrounds almost all part of the insertion member inserted into a tabular cavity have the advantage that the portion need not be cleaned after use. However, the cover itself is long enough to complicate its mounting and dismounting procedures. In addition, the long cover needs considerable time to clean.

The second type of cover may be adapted to be disposable but disposable covers are expensive and increase the medical cost paid by patients.

Another problem with the tip cover of Unexamined Published Japanese Patent Application (kokai) Hei. 4-314439 is that since the tip cover which is rigid is fitted over the tip forming member which is also rigid, rattling is unavoidable. If the tip cover is displaced due to rattling, it may potentially limit the visualized areas accessible to the examiner.

If the tip cover is adapted to fit tightly over the tip forming member, extreme difficulty will be involved in the procedure of mounting and dismounting the tip cover and the excessive force that is applied may potentially damage or distort the cover.

Under the circumstances, the assignee already filed Japanese Patent Application Hei. 6-118153 in 1994 and proposed an endoscope that could solve the aforementioned problems. As shown in FIG. 20, insertion member of the endoscope that is to be inserted into a tubular cavity and which is indicated by a has a tip forming member b which is covered with a tip cover c that is made of an elastic material and which is detachably slipped over the tip forming member b from the distal end.

The part a also has a portion d that permits detachable engagement with the tip cover c which is also provided with a reinforcement plate e on a lateral side.

In order to mount the tip cover c over the tip forming member b or dismount it from the latter, the operator may simply manipulate the cover with a finger put on a guide area while ensuring against damaging the cover c and the fragile parts upstream of the tip forming member b. In addition, the elastic deformation of the tip cover c provides ease in its mounting and dismounting procedures.

In spite of these advantages, the endoscope of Japanese Patent Application Hei. 6-118153, supra, has the limitation that the detachable tip cover is formed of an elastic material and, hence, must be reinforced with plate e on a lateral side. If the tip cover c is pushed with a finger f that is urged against its distal end at an angle with the longitudinal axis, the reinforcement plate e will be lifted by the principle of the lever as indicated by the single dashed line in FIG. 20 and, in the worst case, the tip cover c can potentially be dislodged from the tip forming member b.

Further, generally the structure at the periphery of a forceps holder of the endoscope is much complicated. When the tip cover is detached, it is easy to operate a brushing and cleaning only exposed portions of the forceps holder. However, it is still difficult to clean the sliding surface of the forceps holder with a tip body of the endoscope, i.e., the side surface of the forceps holder, even if the tip cover is detached.

SUMMARY OF THE INVENTION

The present invention was made in view of the foregoing difficulties accompanying the conventional endoscopes. Therefore, an object providing an endoscope having a detachable tip cover that can safely be mounted or dismounted without damaging the endoscope, particularly, the coverings of the curved portion upstream of the tip forming member and which yet can be handled in such a positive manner that even if an extra force is exerted inadvertently, it will be neither lifted nor dislodged from the distal end.

Another object of the invention is to provide an endoscope capable of easily brushing and cleaning peripheral portions of a forceps holder, especially the side surface of the forceps holder, by ejecting liquid detergent or disinfectant sufficiently to the side surface of the forceps holder.

The above and other objects of the invention can be attained by an endoscope with a detachable tip cover which has at the distal end a tip forming member and a forceps holder that is pivotally mounted in the tip forming member, the detachable cover being made of an elastic material and detachably mounted over the distal end in such a way as to cover at least part thereof, the endoscope also having means for mounting the detachable cover at the distal end, characterized in that the detachable tip cover is provided with a reinforcement member which has a portion that can be fitted into engagement with at least part of the mounting means.

When the detachable cover having the reinforcement member is fitted into engagement with the tip forming member, the reinforcement member will cover the tip forming member and, what is more, the two members are brought into mutual engagement, thereby ensuring that the detachable cover will be neither displaced nor dislodged from the tip forming member.

BRIEF DESCRIPTION OF THE DRAWINGS

FIG. 3 shows the general layout of the endoscope of the first example;

FIG. 4 is a side view showing, in longitudinal section, the distal end portion of the endoscope of the first example;

FIGS. 5a and 5b show the mechanism of the cockup manipulator used in the first example;

FIG. 17a is a perspective view showing another example of the forceps holder in an unassembled state, FIG. 17b is a plan view of the forceps holder and, FIG. 17c is a side view of the forceps holder;

FIG. 18 is a perspective view showing yet another example of the forceps holder in an unassembled state;

DESCRIPTION OF THE PREFERRED EMBODIMENTS

Figure 1:
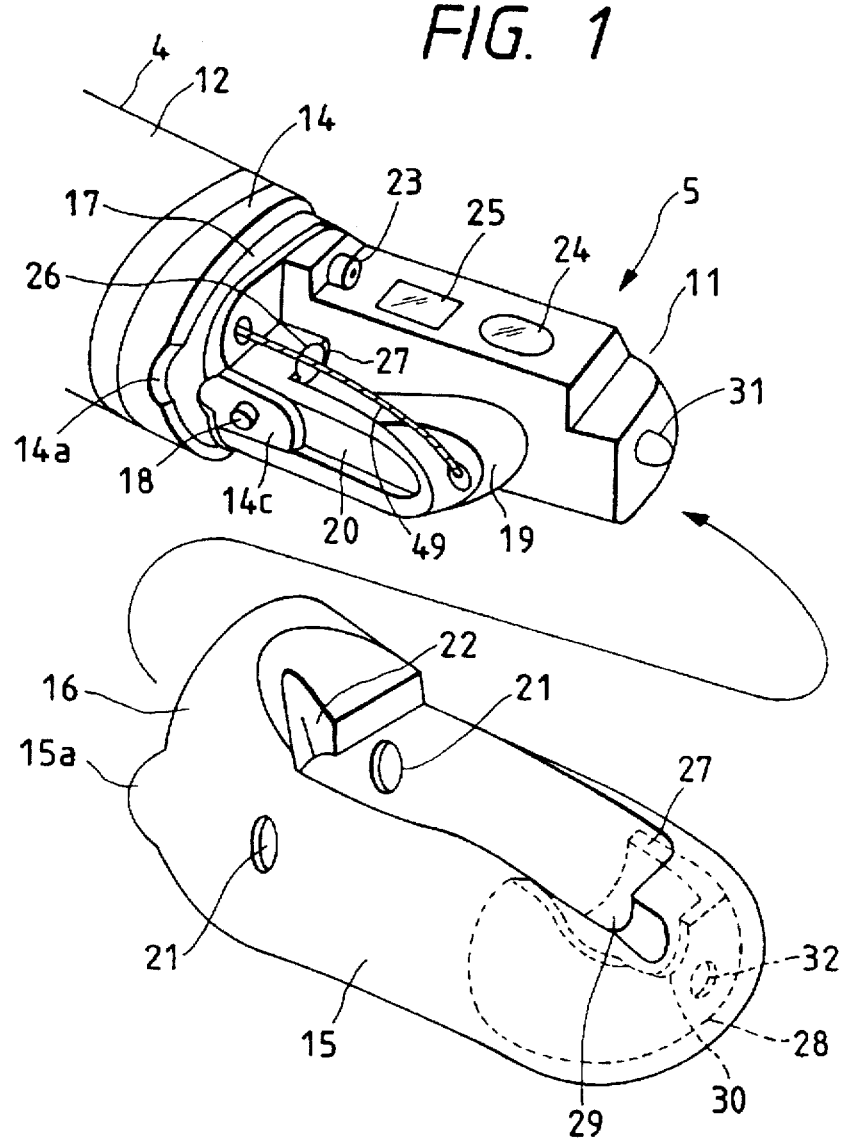
FIG. 1 is a perspective view showing, in an unassembled state, the distal end portion of an endoscope with a detachable tip cover according to the first example of the invention.

Several examples of the invention will now be described with reference to accompanying drawings.

FIGS. 1–6 show a first example of the invention, with FIG. 3 showing the general aspect of an electronic endoscope. As shown, the endoscope generally indicated by reference numeral 1 consists basically of a manipulating portion 2, a slender and flexible insertion member 3 inserted into a tubular cavity in the human body, a tip forming member 5 provided at the distal tip of the portion 3 via a curved portion 4, manipulating knobs 6 that are provided in the manipulating portion 2 for bending the curved portion 4 in specified directions, and a universal cord 7 extending from the manipulating portion 2. The universal cord 7 is provided at the distal end with a light source unit (not shown) and a connector 8 to be connected to a video processor.

Figure 2:
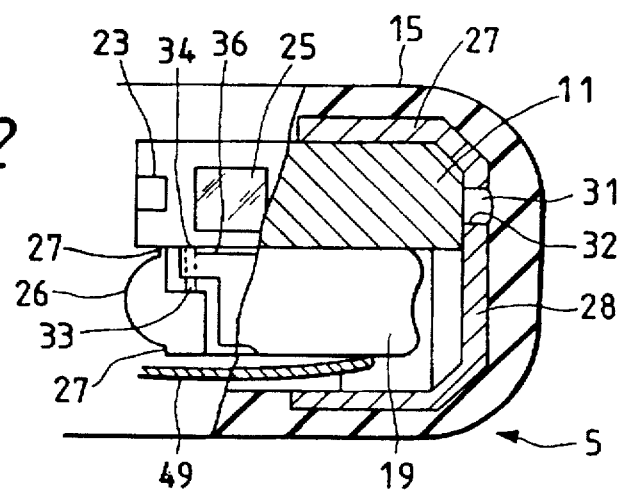
FIG. 2 is a plan view showing, in partial cross section, the distal end portion of FIG. 1.

FIGS. 1 and 2 show the tip forming member 5 in detail. The body of the tip forming member 5 is indicated by 11 and made of a metallic material. The basal end of the body 11 is connected to a curved tube 12 that composes the curved portion 4. The body 11 also has a grip portion 14 provided on the circumference in an area near the connection to the curved tube 12. A detachable tip cover 15 made of an elastic material is adapted such that it can be mounted over the body 11.

The grip portion 14 has a relief 14a in a position that faces a wall extension 15a of the tip cover 15 which is to be described below in greater detail. The grip portion 14 has an overlap 17 formed on its entire circumference in such a way that when the tip cover 15 is mounted over the body 11, the overlap 17 will be situated inside the rear end 16 of the tip cover 15. The overlap 17 is formed in a width of about 1.5 mm and serves to insure that the somatic layer of the patient will not be damaged by high-frequency leakage that would occur if there was a gap between the body 11 of the tip forming member 5 and the rear end 16 of the tip cover 15. If possible, the overlap 17 desirably has a width of at least 1 mm.

The grip portion 14 has an extension on both sides of the distal end of the body 11, with an engagement pin 18 projecting from each extension 14c. The engagement pins 18 protrude in opposite directions from the body 11 to achieve balanced control over the directions of tip rotation, the ease of mounting the tip cover and prevention of its accidental dislodging. One of the two extensions 14c has a forceps holder 19 provided adjacent thereto and the extension 14c which is the closer to the forceps holder 19 is buried in a groove 20 in the body 11 so as to reduce the diameter of the tip forming member 5.

The tip cover 15 has engagement holes 21 formed in positions that face the engagement pins 18. To assure strong engagement, the already-mentioned wall extension 15a is provided at the rear end of the tip cover 15 in two areas that are near the respective engagement holes 21. The tip cover 15 is formed of a biocompatible and electrically insulating material such as silicone or fluorine rubber. In order to provide ease in its mounting and dismounting operations and to assure sufficient strength to prevent its failure during examination in a case, the tip cover 15 is formed in a wall thickness of about 0.5–3 mm.

The tip cover 15 has an insulating portion 22 as an integral part that prevents the occurrence of a spark when a high-frequency knife contacts the body 11. The tip cover 15 has a grained surface that provides good slip without sticking to the somatic layer of the patient. The tip cover 15 has such an inside diameter that its ratio to the outside diameter of the body 11 is in the range from 0.7 to 1 and, hence, the elastic cover 15 can be sufficiently tightened onto the body 11 to prevent rattling, displacement and dislodging.

The body 11 of the tip forming member 5 has a nozzle 23 for cleaning a lens surface, illumination optics 24 and imaging optics 25 which are to be described later in this specification. The body 11 also has a relief 26 which, when the forceps holder 19 is brought to a cock-up position, ensures against the pinching of a forceps (not shown) inserted into aspiration ducts 65 to be described later in this specification. The relief 26 is generally formed as a hemisphere, with a flat portion 27 formed in diametric positions to insure that the forceps holder 19 will not bite into the relief 26 when the holder 19 is brought to a cock-up position.

The tip cover 15 has at the distal end a reinforcement member 28 that is generally shaped like a cup and which has a cylindrical portion 27. The reinforcement member 28 has an opening 29 in the top, with a recess 30 being formed in such a way as to secure smooth insertion of a medical instrument (not shown) and tight fit onto the body 11 of the tip forming member 5. The reinforcement member 28 may be formed of a corrosion-resistant material. Preferably, the reinforcement member 28 is shaped by bending a sheet of stainless steel.

The body 11 also has an engagement projection 31 formed at the distal end in a position offset from the central axis of the body 11. The projection 31 is so adapted that it will engage a corresponding hole 32 in the reinforcement member 28.

The engagement between the projection 31 and the hole 32 ensures against rotation of the tip cover 15 about the tip forming member 5. The hole 32 also serves as temporary fixing means which prevents the occurrence of any molding defects such as the displacement of the reinforcement member 28 during the molding of the tip cover 15, which will eventually become exposed on the outer surface of the molded part or misplaced in it. It should be mentioned that prior to molding, the reinforcement member 28 is coated with a primer in all areas to be covered with an elastic member so that no gaps will form between the elastic member and the reinforcement member 28, thereby preventing subsequent microbial growth.

As shown in FIG. 2, the basal end of the forceps holder 19 is hinged on a pin 33 such that it is pivotal with respect to the body 11. The area of the forceps holder 19 that is close to the pin 33 is spaced from the body 11 by a clearance 35 of about 0.1–0.4 mm, except in an anti-tilt portion 34. The gap 35 contributes to an improvement in the efficiency of cleaning and disinfecting operations since a liquid detergent or disinfectant can be injected into the gap.

As shown in FIG. 4, the body 11 of the tip forming member 11 is fitted into engagement with the reinforcement member 28 in a specified area 36, which has a smaller diameter than the corresponding area of the tip cover 15 which is indicated as a mounting portion in FIG. 4.

We now describe the illumination optics 24 provided on the body 11. As shown in FIG. 4, the body 11 has an entrance 39 through which a bundle of lightguide fibers 38 is to be inserted from the rear end. A prism 41 is provided in a position that is in substantial contact with the exit end face 40 of the fiber bundle 38. All surfaces of the prism 41 except the entrance end face 41a and the exit end face 41b are coated with an evaporated metal such as aluminum to prevent loss due to light diffusion. A light guiding lens 42 typically composed of a single fiber is bonded to the exit end face 40b of the prism 41. The other end of the light guiding lens 42 is bonded to an illuminating lens 43. The prism 41, the light guiding lens 42 and the illuminating lens 43 are contained in an optics mounting hole 44 made generally normal to the hole 39. This arrangement obviates the need to make a lateral hole in the outer surface of the body 11 for mounting the fiber bundle 38, thereby offering the advantage of eliminating the possibility of water leakage.

FIGS. 5a and 5b show a manipulator provided in the manipulating portion 2 for cocking up the forceps holder 19. A cock lever 45 is coupled to an end of a coupling member 46 and the other end of the member 46 is connected to a wire connector 47. The wire connector 47 is connected to a wire 49 via a connecting rod 48 and the wire 49 is passed through the slender and flexible portion 3 to be connected to the forceps holder 19.

The wire connector 47 is provided in such a way that it can be moved back and forth through a U-shaped guide member 50 and the wire 49 is guided by a tube 51 through the portion 3 such that it is moved over the distance from the body 11 of the tip forming member 5 to the guide member 50. Needless to say, both the portion 3 and the tube 51 are rendered airtight in their interior. A coil 52 is wound around the tube 51 to insure that the latter will neither expand nor contract nor buckle. The tube 51 and the coil 52 are connected to a moving block 53 at the end of the manipulating portion 2.

The moving block 53 is provided with a slider 54 capable of moving back and forth with respect to the guide member 50, a cleaning tube 55 connected to a cleaning fixture (not shown), and an O-ring 56 serving as seal means to prevent the leakage of a liquid detergent into the manipulating portion 2. The moving block 53 is so adapted that as the wire connector 47 is moved back and forth, it is pushed accordingly to move the tuber 51 and the coil 52 back and forth.

The wire connector 47 also has an annular groove 57 provided in an area substantially at the center of its length. The annular groove 57 has a click mechanism 58 that is composed of a leaf spring mounted on the guide member 50 and which can be brought into engagement with or disengaged from the groove 57. The annular groove 57 and the click mechanism 58 are provided at the border between a first and a second stroke of action to be described hereinafter.

Figure 6:
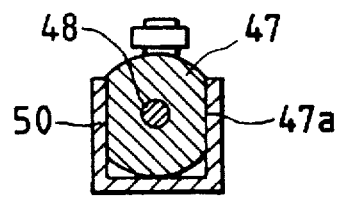
FIG. 6 is a section taken along line V1—V1 of FIG. 5.

As shown more specifically in FIG. 6, the wire connector 47 has a flat portion 47a formed on both lateral sides to insure that when it is moved back and forth through the guide member 50, it will not rattle in the direction of the rotation of the guide member 50 or in directions generally perpendicular to the axis of its movement. As a result, the forceps holder 19 will respond, without play, to the action of the cockup lever 45, thereby increasing the positivity in the examination of the patient.

As shown in FIG. 5a and 5b, the guide member 50 and the wire connector 47 have two strokes of action, the first stroke A for bringing the forceps holder 19 from a maximum cockup position to a prove position and the second stroke B for lowering the prove forceps holder 19 to a position where it is almost exposed from the body 11 of the tip forming member 5. The first stroke A suitably has a distance of about 10 mm and the second stroke B a distance of about 2–10 mm. The endoscope of the first example under consideration is of a right-angle viewing type but it may be of a head-on viewing type.

Figure 7:
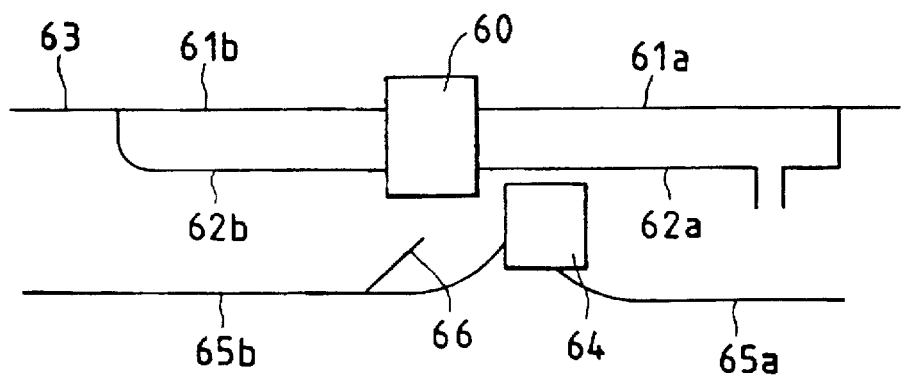
FIG. 7 is a schematic representation of an air/water supply duct.

FIG. 7 shows the general layout of the ducts through the electronic endoscope 1. An air/water supply control section 60 is connected to an air supply duct 61a and a water supply duct 62a which are both within the universal cord 6, an air supply duct 61b and a water supply duct 62b which are both within the insertion member 3, and an air/water supply duct 63 which is the combination of 61b and 62b. An aspiration control unit 64 is connected both to an aspiration duct 65b that has a forceps receptacle 66 and which is positioned on the side where the insertion member 3 is provided and to another aspiration duct 65a positioned on the side where the universal cord 7 is provided.

Figure 8:
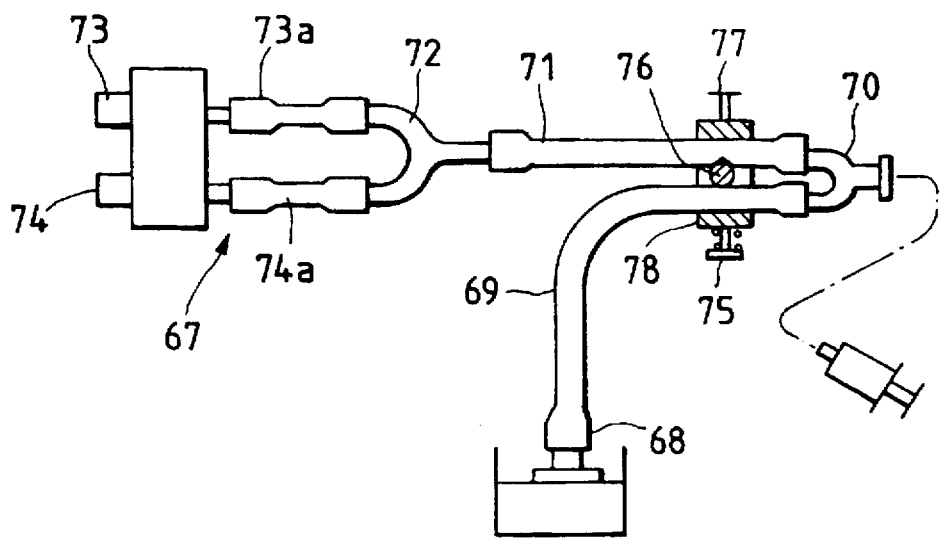
FIG. 8 is a schematic representation of a duct cleaner.
Figure 9:
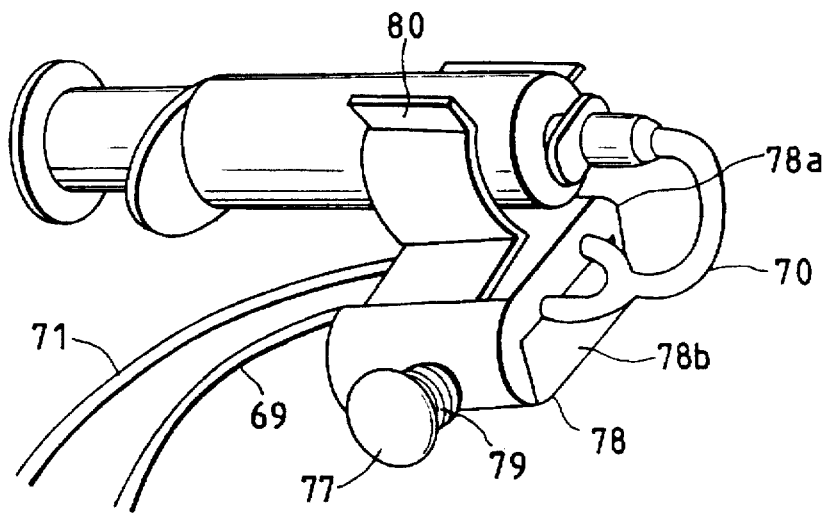
FIG. 9 is a perspective view of a duct switching device.

FIGS. 8 and 9 show a cleaner 67 for pumping a liquid detergent or disinfectant into the ducts mentioned above. An inlet 68 for aspirating a liquid detergent or disinfectant is connected to a first tube 69 which in turn is connected to a fixture 70 that also serves as a branching means and to which water injecting means such as a syringe is to be connected. The fixture 70 is also connected to a water injecting second tube 71 which in turn is connected to a downstream branch 72 which is connected via intermediate tubes 73a and 74a to fixtures 73 and 74, respectively, which are to be mounted on the air/water supply control section 60 and the aspiration control unit 64.

Duct switching means 75 is provided near the fixture 70. It is composed of the following three parts: a depressing portion 76 provided between the first tube 69 and the second tube 71 such that it depresses either one of these tubes to block fluid passage; a manipulating mechanism 77 for actuating the depressing portion 76; and a body 78 mounted slidably along the manipulating mechanism 77 for holding the first tube 69 and the second tube 71.

As shown in FIG. 8, the body 78 consists of two parts 78a and 78b, which can be separated apart to remove the first tube 69 and the second tube 71. The manipulating mechanism 77 and the body 78 are equipped with an urging member 79 which normally depresses the first tube 69. The duct switching means 75 may have a water-supply means holder 80 as an integral part such that water supply means can be mounted or dismounted depending on the need. The first tube 69 and the second tube 71 in the cleaner 67 are typically formed of silicone; the body 78, the manipulating mechanism 77, the depressing portion 76 and the fixtures 74 and 74 are typically formed of materials such as polysulfones and stainless steel that can withstand sterilization with an autoclave or ethylene oxide gas.

Figure 10:
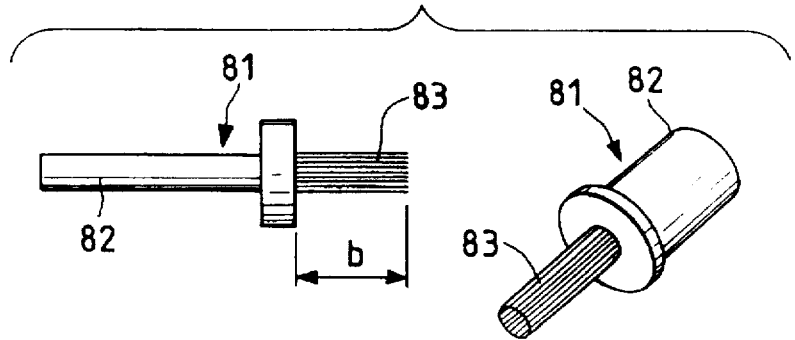
FIG. 10 is a perspective view of a tip brush for cleaning the area around a forceps holder.
Figure 11:
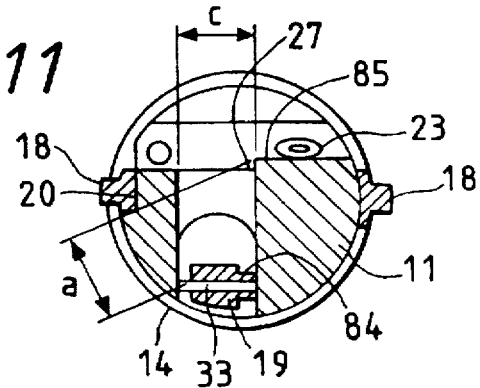
FIG. 11 is a cross section of the tip forming member incorporating the forceps holder.

FIG. 10 shows a tip brush 81 for cleaning the areas of the body 11 of the tip forming member 5 around the forceps holder 19. A grip 82 composed of a comparatively rigid material has bristles 83 provided at the distal end. As shown in FIG. 11, the base 84 of the forceps holder 19 where it joins to the body 11 is recessed and it is limited by the body 11 at both ends and, hence, it is not easily accessible by the bristles 83. Typically, the top surface 85 of the body 11 is spaced from the base 84 of the forceps holder 19 by a distance of about 7 mm. However, if the length h of the bristles 83 is just 7 mm, the body 11 will be damaged by the base of the bristles 83 and yet the bristles 83 can barely touch the area to be brushed; this is hardly effective in achieving the intended cleaning. Therefore, the tip brush 81 used in the first example under consideration has the bristles 83 provided over a length b of at least 8 mm.

The bristles 83 are provided in an area over a width slightly smaller than the width of the body 19. The appropriate thickness of the bristles is about 0.2–1 mm in diameter and their length is optimally about 13 mm which can achieve good balance between the cleaning effect and the protection of the body 11. The tip brush 81 is composed of a material resistant to autoclaving, as exemplified by polyamide resins.

Figure 12:
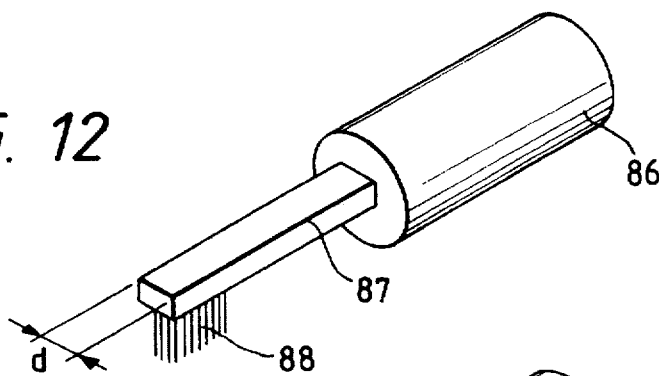
FIG. 12 is a perspective view of another tip brush for cleaning the area around the forceps holder.

FIG. 12 shows another example of the tip brush. A rigid grip 86 has a slender core 87 which in turn is provided with bristles 88 in the distal end portion. The forceps holder 19 in current use typically ranges from about 4.2 to 2.8 mm in width c. Hence, the slender core 87 carrying the bristles 88 has a width d which is set to be no greater than 4.2 mm and this provides easy access to the base 84 of the forceps holder 19, thereby insuring easy brushing of the latter.

Figure 13:
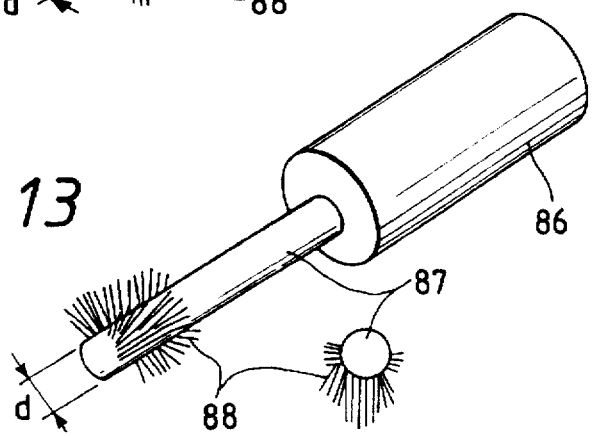
FIG. 13 is a perspective view of yet another tip brush for cleaning the area around the forceps holder.

If desired, the bristles 88 may be provided not only on one side of the core 87 but also on other sides as shown in FIG. 13. Optionally, the bristles 88 may be provided on the entire circumference of a cylindrical core. In these alternative cases, the entire lateral dimension of the bristles as measured across the diameter of the core is suitably designed to be longer than the width of the forceps holder 19 by about 1–4 mm.

We now describe various aspects of the operation of the endoscope furnished with a detachable tip cover in the manner described on the foregoing pages. Let us first explain the procedure of mounting the tip cover 15 over the body 11 of the tip forming member 5. The cover 15 is slipped over the body 11, with its rear end 16 coming first, until the body 11 is fitted in the cylindrical portion 27 of the reinforcement member 28. As the cover 15 is further moved, the rear end 16 rides over the engagement pins 18 to cover the overlap 17 and the engagement projection 31 is fitted into the corresponding hole 32. Upon further movement of the cover 15, the rear end 16 contacts the grip portion 14 and the engagement pins 18 are fitted into the corresponding holes 21, whereby the process of mounting the tip cover 15 over the body 11 is completed.

To assemble the illumination optics, an adhesive coat (not shown) is applied to the entire circumference of the fiber bundle 38 and the bundle is inserted to a specified position in the hole 37. Then, the light guiding lens 42 is bonded to the illuminating lens 43 and the exit end face 41b of the prism 41 is bonded to the light guiding lens 42. Thereafter, an adhesive is applied to the inner surface of the optics mounting hole 44, and the prism 41, the light guiding lens 42 and the illuminating lens 43 are inserted into the hole 44 and fixed therein.

The forceps cockup mechanism and the cleaner are operated in the following manner. When the cockup lever 45 is actuated, the wire 49 is moved back and forth and the forceps holder 19 pivots about the hinge pin 33 to reciprocate between UP and DOWN positions. Stated more specifically, when the forceps holder 19 in the UP position (for maximum cockup) is moved by the first stroke A, it is brought to a prove position; if the cockup lever 45 is further pushed in by the second stroke B, the forceps holder 19 moved below the body 11 until it is almost exposed in the exterior. Upon further pushing of the cockup lever 45, the moving block 53 is pushed and the tube 51 is pushed into the insertion member 3. The relative lengths of tube 51 and wire 49 are such that if the tube 51 becomes shorter than the wire 49, the latter will of course project beyond the tube 51. This means that by pushing in the moving block 53, the forceps holder 19 is shifted to a further lowered position, thus providing ease in the subsequent cleaning operation.

To clean the areas of the body 11 around the forceps holder 19 and the interior of the tube 51, the operator first removes the tip cover 15 from the body 11. Care must be taken here to remove the engagement pins 18 from the corresponding holes 21 before pulling out the cover 15. In the next step, the insertion member 3 is washed under running water with gauze or the like. Then, the areas around the forceps holder 19 are cleaned with the tip brush 81. Care must also be taken here to lower the forceps holder 19 below the body 11 before brushing is made so that the sliding surfaces of the body 11 and the forceps holder 19, the gaps between these two parts and any other normally "inaccessible" areas can be effectively cleaned.

In addition, a syringe or some other suitable device is used to apply a jet of cleaning eater onto areas around the forceps holder 19, particularly the hinge pin 33 and the gap 35, so that any contamination of the gap 35 is washed off. The next step is cleaning the inside of the tube 51. Using a syringe or some other suitable device that is connected to a cleansing fixture (not shown), a liquid detergent is supplied to clean the interiors of both the cleaning tube 55 and the tube 51. Since the inside diameter (I) of the tube 51 is greater than the outside diameter (O) of the wire 49, the latter is off-centered in the tube 51. In this situation, the liquid detergent is mostly supplied to the area where the tube 51 is sufficiently separated from the wire 49 and the areas where they are close to each other cannot be effectively cleaned. To avoid this problem, the cleaner used in the first example is so adapted that by moving the wire 49 back and forth after or during the supply of the liquid detergent, the relative positions of the tube 51 and the wire 49 are changed to assure positive cleaning.

Stated more specifically, the liquid detergent is first supplied by means of a syringe or the like, then the wire 49 is moved back and forth to change its position in the tube 51 and, thereafter, the liquid detergent is supplied again; in this way, inaccessible areas are eliminated to improve the efficiency of the cleaning operation. The same result can be attained by moving the cockup lever 45 back and forth during the supply of the liquid detergent.

The operation proceeds to the cleaning of other ducts using the cleaner 67. To this end, the fixtures 73 and 74 are connected to the air/water supply control section 60 and the aspiration control unit 64, respectively, and a liquid detergent is injected through the inlet 68. By pushing in the manipulating mechanism 77 in counteraction against the urging member 79, the detergent flow is switched from one duct to the other and the liquid detergent is aspirated by detergent supply means; thereafter, the manipulating mechanism 77 is released and the detergent flow is switched back to the first duct in compliance with the action of the urging member 79 and the liquid detergent is supplied by the supply means; subsequently, a liquid detergent or the like is fed into the air/water supply duct. After repeating this procedure several times, the liquid detergent is replaced by air which is blown into the ducts to remove water.

The next step is disinfection, which is performed by immersing the electronic endoscope 1 in a liquid disinfectant. Thereafter, the same disinfectant is fed into the tube 51 as in the cleaning step. Similarly, the liquid disinfectant is injected into the other ducts using the cleaner 67. Then, the forceps holder 19 is lowered to be positioned below the body 11 and almost all surfaces of the forceps holder 19 are contacted with the liquid detergent. In addition, a syringe is used to blow the liquid detergent onto the areas around the body 11 and the forceps holder 19 to insure that there will be no air bubble left in those areas. By lowering the forceps holder 19 to a position where it is substantially exposed from the body 11, it can be positively contacted with the liquid detergent; furthermore, by using the syringe to blow off the air bubbles deposited on body 11 or forceps holder 19, the positivity of the cleaning step can be significantly improved.

As described on the foregoing pages, the tip cover 15 is furnished with the reinforcement member 28 and the body 11 of the tip forming member 5 is fitted into this reinforcement member; this insures that even if the tip cover 15 is pushed under an applied stress, it will not become loose or displaced or otherwise change its position but, instead, it will be positively held in engagement with the body 11 of the tip forming member 5, thereby assuring safety during examination.

As a further advantage, the outer surface of the body 11 need not be provided with grooves and other means for assisting in the mounting of the lightguide fibers and this eliminates the occurrence of water leakage. In addition, the forceps holder 19 is adapted to be movable to a position where it is substantially exposed from the body 11 and this provides ease in cleaning the area where the body 11 faces the forceps holder 19. What is more, almost all surfaces of the forceps holder 19 can be contacted with a liquid detergent and this improves the positivity of disinfecting operations.

It should also be mentioned that the internal structure of the air/water supply duct, particularly the duct switching means, is simple enough to reduce the possibility that air bubbles will be entrapped in the duct; therefore, efficient disinfection can be accomplished by injecting a liquid detergent without forming air bubbles that will get into the duct through the endoscope.

Figure 14:
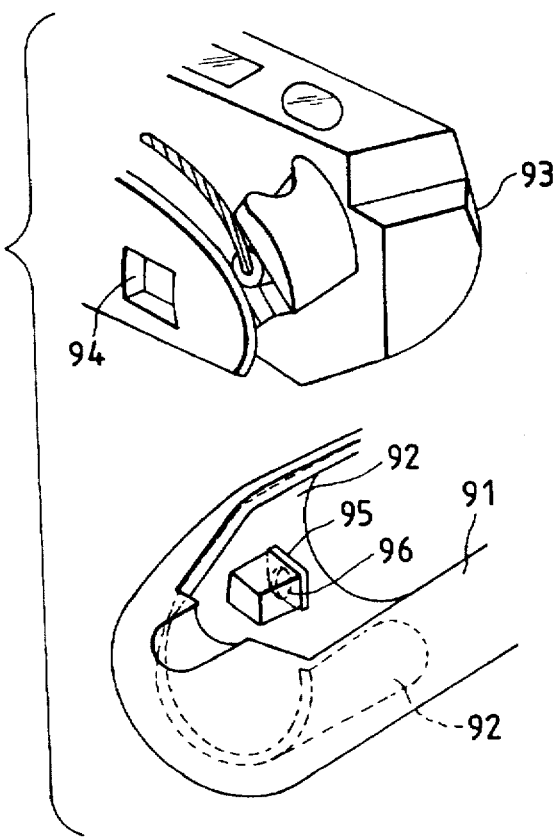
FIG. 14 is a perspective view showing, in an unassembled state, the distal end portion of an endoscope with a detachable tip cover according to the second example of the invention.
Figure 15:
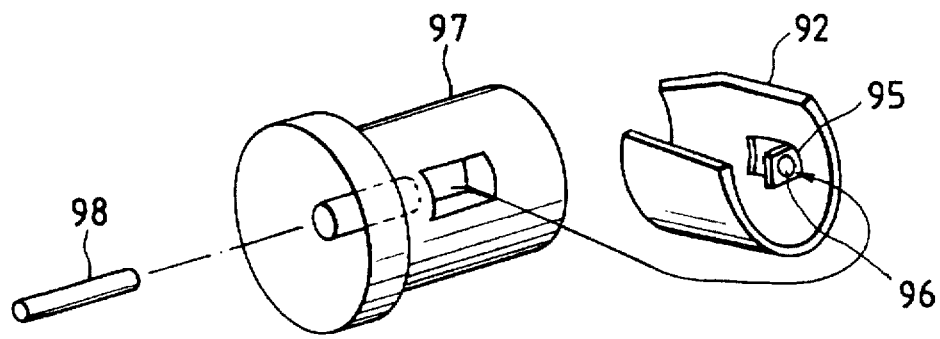
FIG. 15 is a perspective view of a mold for use in the second example.

FIGS. 14–16 show a second example of the invention. A tip cover indicated by 91 in FIG. 14 is furnished with a reinforcement member 92 that is shaped by bending a sheet of a corrosion-resistant material such as stainless steel. The body of a tip forming member which is indicated by 93 has an engagement hole 94 provided in a side wall of the body 93. The reinforcement member 92 within the tip cover 92 has a lug 95 which will engage the hole 94.

The lug 95 has a temporary fixing hole 96, through which a fixing pin 98 on a mold 97 (see FIG. 15) is to be inserted to secure the reinforcement member 92 in position. Since the lug 95 has a non-circular cross section, the reinforcement member 92 can be positively secured to the mold 97 such that it will not be displaced as a result of turning about the lug 95.

Figure 16A:
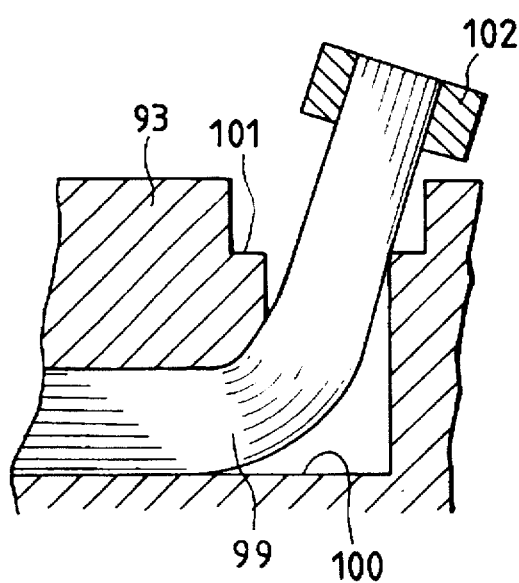
FIGS. 16a and 16b are side views showing, in longitudinal section, the tip forming member of the endoscope of the second example according to the sequence of assembling illumination optics.
Figure 16B:
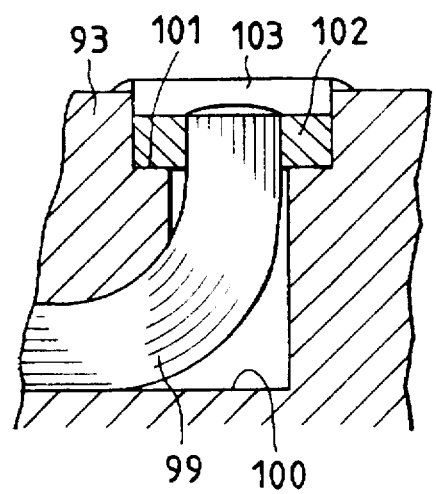

As FIG. 16a and 16b show, the body 93 has a hole 100 through which a bundle of lightguide fibers 99 is to be inserted from the rear end of the body 93. The body 93 also has an optical lens mounting hole 101 that communicates with the hole 100 and which is oriented generally perpendicular to it. Thus, the fiber bundle 99 is to be placed within the holes 100 and 101. A molded part 102 is secured to an end face of the fiber bundle 99. An illuminating lens 103 is placed on top of the molded part 102.

To assemble the fiber bundle 99 into the body 93 of the tip forming member, it is first inserted into the hole 100 in such a way that it projects beyond the optical lens mounting hole 101. The projecting fiber bundle 99 is set in a mold (not shown) and subjected to molding; thereafter, an end face of the molding is cut to a specified shape to provide the molded part 102. Subsequently, the fiber bundle 99 is pulled from the other end of the hole 100 such that the molded part 102 is snugly fitted in the hole 101 and the illuminating lens 103 is bonded to the top of the part 102.

FIG. 17a–17c show another example of the forceps holder. The forceps holder generally indicated by 104 consists of two parts 105 and 106. The basal end of the first part 105 hinges on a pin 108 so that it is pivotal with respect to the body 107 of the tip forming member, and a wire 109 is connected to a connector 105a at a distal end.

The first part 105 has a tapered anti-tilt portion 110 projecting from the other distal end to reduce the area of contact with the body 107. The second part 107 has a generally U-shaped channel 111 formed on the underside; it also has a recess 106a formed on a lateral side in such a way that the connector 105a is fitted into engagement with the recess 106a. Thus, the two parts of the forceps holder 104 are adapted such that when the second part 106 is mounted over the first part 105, the U-shaped channel 111 is snugly fitted into engagement with the first part 105, with the connector 105a also fitted snugly into engagement with the recess 106a.

The first part 105, when set in position, leaves a clearance 112 from the body 107 but this is substantially closed by the second part 107 when it is placed over the first part. The forceps holder 104 having the construction described above is formed of a metal or resin material that is resistant not only to corrosion but also against autoclaving and ethylene oxide gas; an example of the metals having these properties is stainless steel and an exemplary resin is a polysulfone.

FIG. 18 shows yet another example of the forceps holder. The forceps holder of this example which is generally indicated by 113 also consists of two parts 114 and 115. The first part 114 has a wire 116 connected thereto and it also has connectors 117 projecting in such a way that they engage the second part 115.

The first part 114 has a fixing hole 119 through which a hinge pin 118 is to be inserted in such a way that it can hinge on the pin to be pivotal with respect to the body 107 of the tip forming member. The second part 115 has guide openings 120 along which the connectors 117 can slide to ensure smooth mounting of the second part over the first part 114.

The bottom of the second part 115 has a lug 122 that will engage a notch 121 in the first part 114. The forceps holder 113 having the above-described construction is formed of a metal or resin material that is resistant not only to corrosion but also against autoclaving and ethylene oxide gas; an example of the metals having these properties is stainless steel and an exemplary resin is a polysulfone.

The forceps holders 104 and 113 have the advantage that since the second part 106 or 115 can be removed independently for cleaning the endoscope, the clearance between the body 107 of the tip forming member and the first part 105 or 114 is increased to enable more efficient cleaning operations.

To assemble the forceps holder 113 by mounting the second part 115 over the first part 114, the connectors 117 on the first part 11 are slipped into the respective openings 120 in the second part 115, which is simply pushed over the first part 114 until the lug 122 engages the notch 121.

Figure 19:
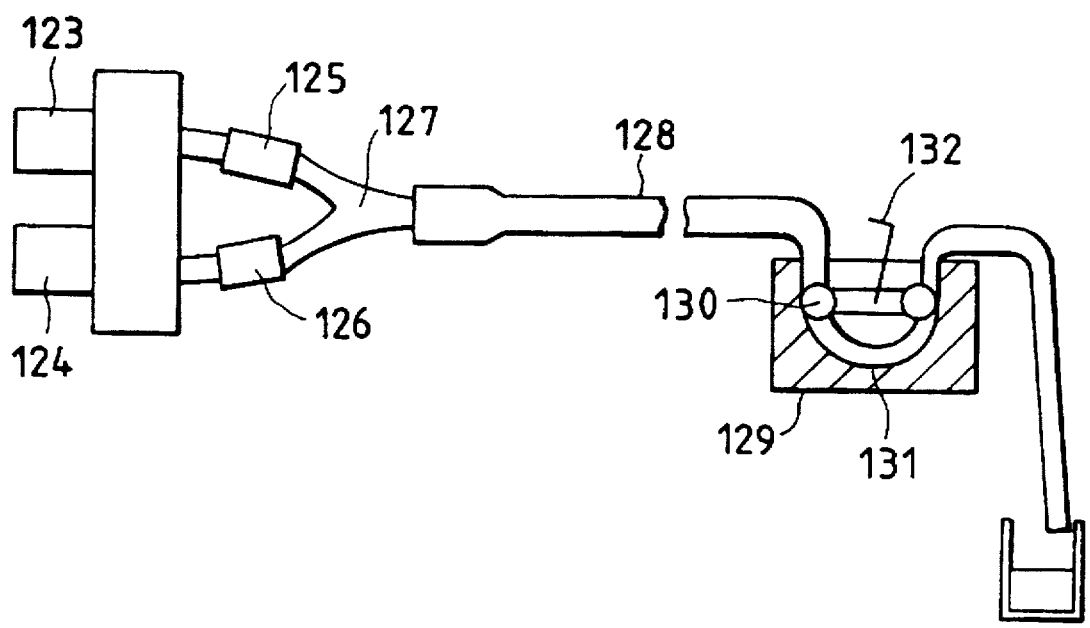
FIG. 19 is a schematic representation of a modified version of the duct cleaner.
Figure 20:
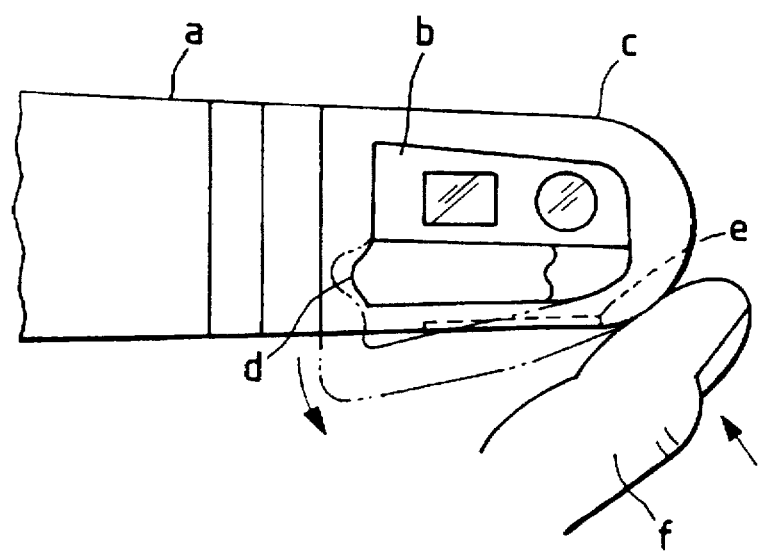
FIG. 20 is a plan view showing the distal end portion of a conventional endoscope with a detachable tip cover.

FIG. 19 shows a modified version of the duct cleaner. Shown by 123 and 124 are fixtures to be connected to the air/water supply control section 60 and the aspiration control unit 64, respectively. The fixtures 123 and 124 are respectively connected to tubes 125 and 126, which converge to be connected to a branch 127. The branch 127 is connected to a comparatively long tube 128 for supplying a liquid detergent. The tube 128 has suitably an inside diameter of about 3–7 mm and a length of about 50 cm–3 m. A pump mechanism 129 is provided in a selected position of the tube 128. The pump mechanism 129 is equipped with a pair of rollers 130 and a guide 131. The purpose of the guide 131 is to insure that the tube 128 in that portion will be compressed to block the fluid flow by means of the rollers 130. The pump mechanism 129 also has a lever 132 connected to the rollers 130. By turning the lever 132, the rollers 130 will rotate to permit injection of a liquid detergent or disinfectant.

Stated more specifically, the fixtures 123 and 124 are connected to the air/water supply control section 60 and the aspiration control unit 64, and the tube 128 is immersed in a liquid detergent or disinfectant, and the lever 132 is turned, whereupon the liquid detergent or disinfectant is injected into the duct through the endoscope.

According to the embodiments described above, one aspect of the present invention provides the apparatus or devices recited as follows:

(a) An endoscope with a detachable tip cover which has at the distal end a tip forming member and a forceps holder that is pivotally mounted in the tip forming member, the detachable tip cover being made of an elastic material and detachably mounted over the distal end in such a way as to cover at least part thereof, the endoscope also having means for mounting the detachable cover at the distal end, characterized in that the detachable tip cover is provided with a reinforcement member which has a portion that can be fitted into engagement with at least part of the mounted means.

In the endoscope as recited above, the engagement between the reinforcement member and the mounting means is established by at least two areas of contact, the reinforcement member is fitted into engagement with the body of the tip forming member by direct contact with each other, the reinforcement member has a generally cylindrical portion in at least part thereof, and the reinforcement member is generally in the shape of a cup having a bottom at the distal end.

In short, the aspect of the invention as described above intend to provide an endoscopes with a detachable tip cover that can safely be mounted or dismounted without damaging the endoscope, particularly, the coverings of the curved portion upstream of the tip forming member and which yet can be handled in such a positive manner that even if an extra force is exerted inadvertently, it will be neither lifted nor dislodged from the distal end.

According to the embodiments described above, another aspect of the present invention provides the apparatus or devices recited as follows:

(b) A right-angle viewing endoscope having imaging optics and illumination optics in a tip forming member, the illumination optics comprising an insertion hole made in the tip forming member along the axis of the insertion member of the endoscope which is to be inserted into a tubular cavity in the human body, a bundle of lightguide fitted into the insertion hole, an optics mounting hole that communicates with the insertion hole and which is oriented in the radial direction of the insertion member, optical axis tilting means that is situated within the optics mounting hole in a position opposing the distal end face of the fiber bundle, and light guiding means and an illuminating lens that are provided on the exit side of the optical axis tilting means.

In the right-angle viewing endoscope as recited above, the optical axis tilting means is a prism, the prism is coated with an evaporated metal on all outer surfaces except the entrance face opposing the fiber bundle and the exit face opposing the light guiding means, the metal to be evaporated is aluminum, and the optical axis tilting means is a mirror.

In short, the aspect of the invention recited above aims at providing illumination optics in the tip forming member of a right-angle viewing endoscope that will not undergo water leakage during cleaning operations or after receiving impacts and which yet suffers from only limited loss in the quantity of light.

According to the embodiments described above, the other aspect of the present invention provides the apparatus or devices recited as follows:

(c) An endoscope having a forceps cockup manipulator that comprises a wire connector provided in the manipulating portion of the endoscope and which is connected at one end to a cockup lever, a wire connected to the other end of the wire connector, and a forceps holder connected to the wire, the manipulator being actuated by the action of the cockup lever to pivot the forceps holder via the wire connector and the wire, characterized in that the manipulating portion is provided with rotation regulating means which prevents the rotational movement of the wire connector.

In the endoscope as recited above, the rotation regulating means comprises flat portions formed in the direction in which the wire connector is moved back and forth and a guide member that has flat surfaces to contact the flat portions and which guides the wire connector.

In short, the endoscope recited above aims at improving the response of the forceps holder to the action of the forceps lever.

According to the embodiments described above, still another aspect of the present invention provides the apparatus or devices recited as follows:

(d) A tip brush for cleaning the distal end of an endoscope having a forceps holder, characterized by comprising a comparatively rigid grip, a bristle holder provided adjacent to the grip, and a bundle of bristles not shorter than 7 mm which are provided on the bristle holder.

The tip brush for cleaning the distal end of an endoscope having a forceps holder further comprises a comparatively rigid grip and a bristle holder that has a plurality of bristles in at least one direction and which is not wider than 4.2 mm on each side, the tip brush is made of a material that can be autoclaved, the bristles are made of a polyamide resin.

In short, the tip brush described above assures positive brushing of the areas around the forceps holder in the tip forming member of an endoscope.

According to the embodiments described above, still another aspect of the present invention provides the apparatus or devices recited as follows:

(e) A forceps cockup manipulator comprising a forceps holder that is provided in a tip forming member and which is to be enclosed with a detachable tip cover together with the tip forming member, a wire connector provided within the manipulating portion of an endoscope, a wire connected at one end to the forceps holder and connected at the other end to the wire connector, and a cockup lever provided in the manipulating portion, the wire connector being moved back and forth in response to the action of the cockup lever, whereby the forceps holder pivots with respect to the tip forming member, characterized in that the wire connector is moved back and forth over a stroke that consists of the first stroke for moving the forceps holder from a maximum cockup position to a maximum prone position for the mounting of the tip cover and the second stroke for moving the forceps holder, with the tip cover removed, in a direction opposite to the cockup direction such that the holder is lowered from the maximum prone position for the mounting of the tip cover to a position where the forceps holder is substantially exposed from the tip forming member.

The forceps cockup manipulator as described above has notifying means for indicating the border between the first and second strokes; the notifying means comprises a wire guide member and an urging member provided in contact with the outer surface of a guide member and is capable of changing the working force of the cockup lever; the right-angle viewing endoscope with a detachable tip cover having a tip forming member and a forceps holder at the distal end of the insertion member of the endoscope which is to be inserted into a tubular cavity in the human body, at least part of the tip forming member being covered with the detachable tip cover formed of an elastic member and the forceps holder being raised or lowered by means of a wire in response to the action of a forceps lever provided in the manipulating portion of the endoscope, characterized in that the forceps holder consists of two parts, the first part having a support pivotally connected to the tip forming member and a connector connected to the wire, and the second part detachably connected to the first part; the endoscope having a forceps holder manipulator comprising a forceps holder provided in a tip forming member, a wire connected to the forceps holder at an end, a wire guide channel that encloses the wire and which is situated within the insertion member of the endoscope which is to be inserted into a tubular cavity in the human body, a cockup manipulator provided in the manipulating portion of the endoscope, and a wire connector provided in the cockup manipulator for moving the wire back and forth, characterized by further including wire guide channel moving means by which the wire guide channel is moved back and forth with respect to the insertion member according as the wire connector is moved back and forth; and the wire guide channel moving means depresses the wire guide channel according as the fire connector is moved back and forth.

In short, the aspect of the invention recited right above aims at improving the efficiency of cleaning the gaps between the tip forming member of an endoscope and the forceps holder.

According to the embodiments described above, still another aspect of the present invention provides the apparatus or devices recited as follows:

(f) A duct cleaner comprising a connector connecting fluid supply means for feeding a fluid such as a liquid detergent or disinfectant into the duct of an endoscope, a branch connected to communicate with the connector, a first duct connected to communicate with an end of the branch, a second duct connected to the other end of the branch, a fixture provided at the downstream end of the first duct and connected to the liquid detergent feed inlet of the endoscope, an aspiration inlet provided at the other end of the second duct for aspirating a liquid detergent or disinfectant, and duct switching means provided halfway the first and second ducts for clogging either of the ducts.

The duct switching means comprises a body for holding the first and second ducts, depressing means provided on the body for depressing either the first duct or the second duct, and a manipulating portion for moving the depressing means back and forth; the duct cleaner is made of a material having resistance to autoclaving; and the autoclavable material is silicone, polysulfone or polymethylpentene.

In short, the aspect of the invention recited right above aims at proving a duct cleaner that is protected against the entrance of air bubbles, thereby assuring positive disinfection.

As taught in commonly assigned Japanese Patent Application Hei. 6-118153, supra, the conventional art detachable tip cover for endoscope which is made of an elastic material has a reinforcement plate provided only on a lateral side. If such a tip cover is pushed with a finger that is urged against its distal end at an angle with the longitudinal axis, the reinforcement plate will be lifted by the principle of the lever and, in the worst case, the tip cover can potentially be dislodged from the providing portion of the endoscope. However, according to the present invention, the tip cover need not be fitted into engagement with the entire periphery of the tip forming member and, hence, even if the latter has a special shape, there is no possibility for the tip cover to be displaced or dislodged. The reinforcement member is fitted in such way that it makes direct contact with the tip forming member and this is effective in assuring that the area of contact between the two members can withstand more repetitions of the mounting and dismounting operations of the tip cover and, in addition, the direct contact between the two members ensures against displacement of the tip cover.

Further, according to the invention, the reinforcement member has a cylindrical part and this offers the advantage that the reinforcement member can be fitted to the tip forming member in any desired direction and, hence, in an easy manner. Additionally, both the reinforcement member and the tip forming member can be worked easily. The structure of the reinforcement member is adapted to have a bottom and this contributes to a significant increase in the strength of the reinforcement member.

The illuminating optics for conventional endoscopes are exemplified by those described in Unexamined Published Japanese Utility Model Application (kokai) Hei. 1-77701 and Examined Japanese Utility Model Publication Sho. 52-26902. According to the first reference, a bundle of lightguide fibers molded to a specified bent shape is inserted into the tip forming member of an endoscope through a hole provided in the lower part of the tip forming member and, thereafter, the hole is closed with a lid that is securely bonded to provide watertightness. According to the second reference, optical axis changing means is provided in a position opposing the exit end face of the fiber bundle. However, in the first approach which only bonds a thin sheet of lid to the inlet for the insertion of the fiber bundle which is formed in the tip forming member has the disadvantage that if the tip cover, as removed from the tip forming member, is bumped against a foreign object or if the cover is subjected to repeated cleaning operations, it will be deformed to cause water leakage from the tip forming member. The second approach is also disadvantageous in that due to the large space that exists between the end face of the fiber bundle and the optical axis changing means, as well as between the optical axis changing means and the illuminating lens, not only is it impossible to provide a desired luminous intensity distribution but the scattering of light has also caused a considerable loss in the quantity of light. On the other hand, the present invention assures complete protection against water leakage since there is no need to provide an axial groove in the tip forming member for assisting in the mounting of the fiber bundle. Further, a prism is used as the optical axis tilting means and this is not only effective in reducing the loss of the quantity of light but also instrumental to easy assembly of the illumination optics. In the invention, a metal is evaporated onto the outer surface of the prism and this contributes to a further reduction in the loss of the quantity of light. Aluminum is evaporated and this enables the tilting of the optical axis in an inexpensive and yet effective manner. A mirror is used as the optical axis tilting means and this enables the intended object of the invention to be attained at low cost.

In the conventional art, the forceps holder has been raised or lowered by a method in which wire connector connected to a wire is moved back and forth by means of a coupling member connected to a cockup lever (see Examined Japanese Patent Publication (kokoku) Hei. 2-43488). However, the wire connector itself is not provided with a guide or a rotation preventing means which regulates the tendency of that connector to rotate with respect to the body of the manipulating portion of an endoscope. In other words, the direction in which the coupling member exerts a force on the wire connector does not coincide with the direction in which the latter is moved back and forth and, hence, the connection between the coupling member and the wire connector rattles in the initial period of their operation and the resulting rotation of the wire connector will eventually deteriorate the response of the cocking action. However, according to the present invention, there is no play in the action of the manipulator which raises or lowers the forceps holder and the latter will respond rapidly to the movement of the cockup lever, thereby contributing not only to a better performance in cannulation but also to a shorter time of examination. Further, the invention obviates the need to use a rotation regulating member such as a key slot or a spline, thus making it possible to provide an inexpensive rotation regulating means.

With the conventional endoscopes having a detachable tip cover, no brushes have been available that are specifically intended for cleaning the areas around the forceps holder. In practice, a channel cleaning brush has been used for this purpose but since this is inherently intended for cleaning channels, a sufficient force cannot be applied to the brush. The use of a toothbrush does not solve the problem since it is so wide that it cannot reach the base of the forceps holder and it takes quite a long time to accomplish the desired cleaning. On the other hand, the invention assures that even areas of "limited" access such as the base of the forceps holder can positively be brushed. The brush can be autoclaved for sterilization and the endoscope is effectively protected against contamination with the brush, whereby it is kept in a hygienic state. The brush can also be autoclaved and yet it has a suitable hardness for enabling thorough cleaning.

With endoscopes of a type in which the tip forming member having a forceps holder is enclosed with a tip cover, it has been proposed that a stopper for regulating the stroke of a manipulating wire should be provided to insure that the wire can be further pushed in beyond the position where it is situated when the forceps holder is in a maximum prone position [see Unexamined Published Japanese Patent Application (kokai) Hei. 5-115431]. With the tip cover removed, the outer surface of the forceps holder can be cleaned fairly easily with a brush or some other means; however, the gap between the forceps holder and the tip forming member of the endoscope is narrow and difficult to access by a cleaner such as a brush. Hence, it has taken much time to wash off all debris that has been deposited in the gap between the forceps holder and the tip forming member. However, the cockup manipulator of the invention has no gaps left between the forceps holder and the tip forming member and this not only contributes to a marked improvement in the efficiency of cleaning operations but also allows an increased volume of liquid detergent to be supplied over a unit area, thereby contributing to a higher efficiency of disinfecting operations.

The cockup manipulator has means for notifying the border between the first and the second stroke while the tip cover is being mounted over the tip forming member and this insures that the wire will not be inadvertently pushed in up to the point where the second stroke starts, with the result that the buckling of the wire can be prevented. The invention obviates the need to provide the notifying means of a complex structure in the area around the cockup lever but instead the means is provided at a fairly spacious site; therefore, the cockup manipulator of this invention is easy to design and assemble.

Japanese Patent Application Hei. 3-108879 proposes an endoscope equipped with a detachable forceps holder. The invention provides an improvement over this proposal since a large gap is formed between the forceps holder and the tip forming member and this contributes to a marked improvement in the efficiency of cleaning and disinfecting operations.

In the conventional endoscope, the wire guide channel enclosing a wire is fixed to the manipulating portion and no means is provided that is in operative association with the forceps lever (see Examined Japanese Utility Model Publication (kokoku) Hei. 2-431488). A problem with this endoscope is that if the size of the forceps holder exceeds a certain limit, it fails to become substantially completely exposed from the tip forming member even if the full stroke of the wire connector in the manipulating portion is utilized. Even if the forceps holder is of a common size, the winding of many turns of a loop around the insertion member of the endoscope will pull the wire guide channel to such an extent that the relative stroke of the forceps holder is occasionally too short to enable its movement to the position where it is exposed from the tip forming member. In either case, much time is required to perform thorough cleaning of the gap between the forceps holder and the tip forming member.

However, according to the invention, the stroke of the forceps holder is sufficiently increased to reduce the size of the manipulating portion of the endoscope and yet improve the efficiency in the cleaning of the areas around the forceps holder at the distal end of the endoscope. Additionally, the endoscope is so adapted that the wire guide channel is moved back and forth by means of a wire moving member and this contributes to the realization of an inexpensive structure.

As typically taught in Japanese Patent Application Sho. 58-93855, the duct switching means used in the conventional endoscope comprises valves provided within the ducts. However, this approach requires a complex structure which has a high likelihood to trap air bubbles around the valves. If a liquid disinfectant is injected into ducts containing air bubbles, the latter will get into the duct of the endoscope and must be removed by injecting water for quite a long time.

However, the duct cleaner of the invention features simplicity in the internal structure of conduits and has no areas where there is a potential for the buildup of air bubbles. Therefore, any air bubbles that occur in the ducts can readily be removed and positive disinfection can be accomplished within a shorter time. The invention provides duct switching means of a simple structure. The cleaner is adapted to resist autoclaving and, hence, it can be disinfected in a sufficiently positive manner to ensure that it will not contaminate the endoscope.

As described on the foregoing pages, the tip cover of the endoscope of the present invention is characterized in that the reinforcement member of the cover is attached to the tip forming member in such a manner that the latter is fitted into effective engagement with the former. Therefore, even if the tip cover is pushed with a finger that is urged against its distal end at an angle with the longitudinal axis, it will be neither lifted nor dislodged and the endoscope can be used with utmost safety.

Further, according to the endoscope of the present invention, it is easy to brush and clean the peripheral portions of a forceps holder, especially the side surface of the forceps holder, because the liquid detergent or disinfectant can be ejected sufficiently toward the sliding surface of the forceps holder with a tip body of the endoscope.

Furthermore, as described above, the endoscope of the invention further includes a wire having a first end connecting to the forceps holder and a second end connecting to a wire connecting member formed in the operation member, the forceps holder rotating with respect to the tip providing member by moving back and forth the wire connecting member in response to an operation of a forceps holder lever formed in the operation member, and the wire connecting member moves back and forth in one of a first stroke for bringing the forceps holder from a maximum cockup position to a prove position and a second stroke for lowering the prove forceps holder to a position where it is almost exposed from the body of the tip forming member. Moreover, the endoscope further includes an indicator member for indicating a boundary of the first stroke and the second stroke, and the indicator member comprises an urging member attaching on the wire connecting member and a guide member, the urging member varying an operation force of the forceps holder lever. Accordingly, it is easily brushing and cleaning the peripheral portions of a forceps holder, especially the side surface of the forceps holder, by ejecting liquid detergent or disinfectant sufficiently to the side surface of the forceps holder.

What is claimed is:

1. An endoscope comprising:

a light source;

an insertion member to be inserted into a tubular cavity;

a tip forming member having a body comprising an engagement member, said tip forming member positioning at one end of said insertion member;

an operation member disposed at the other end of said insertion member, said operation member being operatively linked with said tip forming member;

a connector connecting between said light source and said operation member;

a cover which covers at least a part of said body of said tip forming member, said cover being formed of an elastic material; and a reinforcement member disposed in said cover having an engagement member, said engagement member of said reinforcement member engageable with said engagement member of said body of said tip forming member, the reinforcement member being formed of a more rigid material than the cover.

2. The endoscope of claim 1, wherein said cover is detachably mounted on said tip forming member.

3. The endoscope of claim 1, wherein said cover comprises a wall extension at a rear end portion thereof, and said tip forming member comprises a relief at a portion thereof facing said wall extension of said cover.

4. The endoscope of claim 1, wherein said body comprises an overlap portion formed on its entire circumference, a rear inner part of the cover situated on the overlap portion.

5. The endoscope of claim 4, wherein said overlap has a width of at least 1 mm.

6. The endoscope of claim 5, wherein said overlap has a width of about 1.5 mm.

7. The endoscope of claim 1, wherein said reinforcement member is substantially cylindrical.

8. The endoscope of claim 1, wherein said tip forming member comprises an engagement pin and said cover comprises an engagement hole engageable with said engagement pin of said tip forming member.

9. The endoscope of claim 1, wherein said cover is formed of an electrically insulating material.

10. The endoscope of claim 9, wherein said cover is formed of silicone rubber.

11. The endoscope of claim 9, wherein said cover is formed of fluorine rubber.

12. The endoscope of claim 1, wherein said cover is formed in a wall thickness of about 0.5–3 mm.

13. The endoscope of claim 1, wherein said cover comprises an insulating portion as an integral part thereof.

14. The endoscope of claim 1, wherein said cover has a grained surface.

15. The endoscope of claim 1, wherein said cover has such an inside diameter that its ratio to the outside diameter of said body of said tip forming member is in a range from 0.7 to 1.

16. The endoscope of claim 1, wherein said reinforcement member comprises an opening in the top thereof.

17. The endoscope of claim 16, wherein said opening of said reinforcement member comprises a recess.

18. The endoscope of claim 1, wherein prior to molding, said reinforcement member is coated with a primer in all areas to be covered with an elastic member.

19. The endoscope of claim 1, wherein said body of said tip forming member is fitted into engagement with said reinforcement member in a specified area, which has a smaller diameter than the corresponding area of said cover.

20. The endoscope of claim 1, wherein said reinforcement member is formed of a corrosion-resistant material.

21. The endoscope of claim 20, wherein said reinforcement member is shaped by bending a sheet of stainless steel.

22. An endoscope comprising:
a light source;
an insertion member to be inserted into a tubular cavity;
a tip forming member positioning at one end of said insertion member;
an operation member disposed at the other end of said insertion member, said operation member being operatively linked with said tip forming member;
a connector connecting between said light source and said operation member;
a cover which covers at least a part of said body of said tip forming member, said cover being formed of an elastic material; and
a substantially cylindrical reinforcement member disposed in said cover, the reinforcement member being formed of a more rigid material than the cover.

23. The endoscope of claim 22, wherein said tip forming member comprises a body comprising a first engagement member and said reinforcement member comprises a second engagement member engageable with said first engagement member of said body of said tip forming member.

24. The endoscope of claim 22, wherein said cover is detachably mounted on said tip forming member.

25. The endoscope of claim 22, wherein said cover comprises a wall extension at a rear end portion thereof, and said tip forming member comprises a relief at a portion thereof facing said wall extension of said cover.

26. The endoscope of claim 22, wherein said body comprises an overlap portion formed on its entire circumference, a rear inner part of the cover situated on the overlap portion.

27. The endoscope of claim 26, wherein said overlap has a width of at least 1 mm.

28. The endoscope of claim 27, wherein said overlap has a width of about 1.5 mm.

29. The endoscope of claim 22, wherein said tip forming member comprises an engagement pin and said cover comprises an engagement hole engageable with said engagement pin of said tip forming member.

30. The endoscope of claim 22, wherein said cover is formed of an electrically insulating material.

31. The endoscope of claim 30, wherein said cover is formed of silicone rubber.

32. The endoscope of claim 30, wherein said cover is formed of fluorine rubber.

33. The endoscope of claim 22, wherein said cover is formed in a wall thickness of about 0.5–3 mm.

34. The endoscope of claim 22, wherein said cover comprises an insulating portion as an integral part thereof.

35. The endoscope of claim 22, wherein said cover has a grained surface.

36. The endoscope of claim 22, wherein said cover has such an inside diameter that its ratio to the outside diameter of said body of said tip forming member is in a range from 0.7 to 1.

37. The endoscope of claim 22, wherein said reinforcement member comprises an opening in the top thereof.

38. The endoscope of claim 37, wherein said opening of said reinforcement member comprises a recess.

39. The endoscope of claim 22, wherein prior to molding, said reinforcement member is coated with a primer in all areas to be covered with an elastic member.

40. The endoscope of claim 22, wherein said body of said tip forming member is fitted into engagement with said reinforcement member in a specified area, which has a smaller diameter than the corresponding area of said cover.

41. The endoscope of claim 22, wherein said reinforcement member is formed of a corrosion-resistant material.

42. The endoscope of claim 41, wherein said reinforcement member is shaped by bending a sheet of stainless steel.

43. An endoscope comprising:
a light source;
an insertion member to be inserted into a tubular cavity;
a tip forming member positioning at one end of said insertion member;
an operation member disposed at the other end of said insertion member, said operation member being operatively linked with said tip forming member;
a connector connecting between said light source and said operation member;
a cover which covers at least a part of said body of said tip forming member, said cover being formed of an elastic material; and
a reinforcement member disposed in said cover, said reinforcement member coated, prior to molding, with a primer in all areas to be covered with an elastic member, the reinforcement member being formed of a more rigid material than the cover.

44. The endoscope of claim 43, wherein said tip forming member comprises a body comprising a first engagement member and said reinforcement member comprises a second engagement member engageable with said first engagement member of said body of said tip forming member.

45. The endoscope of claim 43, wherein said cover is detachably mounted on said tip forming member.

46. The endoscope of claim 43, wherein said cover comprises a wall extension at a rear end portion thereof, and said tip forming member comprises a relief at a portion thereof facing said wall extension of said cover.

47. The endoscope of claim 43, wherein said body comprises an overlap portion formed on its entire circumstance, a rear inner part of the cover situated on the overlap portion.

48. The endoscope of claim 47, wherein said overlap has a width of at least 1 mm.

49. The endoscope of claim 48, wherein said overlap has a width of about 1.5 mm.

50. The endoscope of claim 43, wherein said reinforcement member is substantially cylindrical.

51. The endoscope of claim 43, wherein said tip forming member comprises an engagement pin and said cover comprises an engagement hole engageable with said engagement pin of said tip forming member.

52. The endoscope of claim 43, wherein said cover is formed of an electrically insulating material.

53. The endoscope of claim 52, wherein said cover is formed of silicone rubber.

54. The endoscope of claim 52, wherein said cover is formed of fluorine rubber.

55. The endoscope of claim 43, wherein said cover is formed in a wall thickness of about 0.5–3 mm.

56. The endoscope of claim 43, wherein said cover comprises an insulating portion as an integral part thereof.

57. The endoscope of claim 43, wherein said cover has a grained surface.

58. The endoscope of claim 43, wherein said cover has such an inside diameter that its ratio to the outside diameter of said body of said tip forming member is in a range from 0.7 to 1.

59. The endoscope of claim 43, wherein said reinforcement member comprises an opening in the top thereof.

60. The endoscope of claim 59, wherein said opening of said reinforcement member comprises a recess.

61. The endoscope of claim 43, wherein said body of said tip forming member is fitted into engagement with said reinforcement member in a specified area, which has a smaller diameter than the corresponding area of said cover.

62. The endoscope of claim 43, wherein said reinforcement member is formed of a corrosion-resistant material.

63. The endoscope of claim 62, wherein said reinforcement member is shaped by bending a sheet of stainless steel.

* * * * *